(12) United States Patent
Jansen

(10) Patent No.: US 8,252,600 B2
(45) Date of Patent: Aug. 28, 2012

(54) PORTABLE MEASURING DEVICE

(75) Inventor: Herbert Peter Jansen, Amsterdam (NL)

(73) Assignee: Hedon Electronic Developments BV, Delft (NL)

( * ) Notice: Subject to any disclaimer, the term of this patent is extended or adjusted under 35 U.S.C. 154(b) by 225 days.

(21) Appl. No.: 12/598,155

(22) PCT Filed: Apr. 29, 2008

(86) PCT No.: PCT/NL2008/000115
§ 371 (c)(1),
(2), (4) Date: Apr. 1, 2010

(87) PCT Pub. No.: WO2008/133499
PCT Pub. Date: Nov. 6, 2008

(65) Prior Publication Data
US 2010/0197036 A1    Aug. 5, 2010

(30) Foreign Application Priority Data
May 1, 2007 (NL) ..................................... 1033784

(51) Int. Cl.
*G01N 31/22* (2006.01)
*G01N 31/00* (2006.01)
(52) U.S. Cl. .......................... 436/163; 422/68.1; 422/50
(58) Field of Classification Search .................. 436/163; 422/68.1, 50
See application file for complete search history.

(56) References Cited

U.S. PATENT DOCUMENTS
5,837,199 A * 11/1998 Dumschat .................... 422/68.1
6,608,493 B2 * 8/2003 Hensler et al. ................ 324/713
6,946,844 B1    9/2005 Colahan et al.

FOREIGN PATENT DOCUMENTS
DE    2847899 A1    5/1980
DE    4242215 C1    5/1994
JP    62-24171    2/1987

OTHER PUBLICATIONS

ISO 8502-6—Preparation of steel substrates before application of paints and related products—Tests for the assessment of surface cleanliness. Part 6: Extraction of soluble contaminants for analysis, The Bresle method, Second Edition (2006).
International Search Report for Application No. PCT/NL2008/000115, dated Aug. 27, 2008.

* cited by examiner

*Primary Examiner* — Christine T Mui
(74) *Attorney, Agent, or Firm* — Nelson Mullins Riley & Scarborough LLP

(57) ABSTRACT

The invention relates to a portable measuring device for measuring the salinity, the acidity (pH) or other chemical and physical parameters on different types of surfaces (9) such as inner and outer surfaces of tubes and surfaces of floors, walls, ceilings and such like, whereby the measuring device comprises electronic circuits (2), a measuring unit and a housing (4) in which a test chamber (10) has been formed, whereby the test chamber is provided with: 1) a first opening that can be positioned against a surface to be tested, 2) a second opening through which a fluid such as de-ionized water can be introduced into the test chamber, 3) a resilient seal (11) for sealing the test chamber there where it is brought against the test surface area, 4) a number of sensors (5) taken up in the test chamber that are connected to the electronic circuits and the measuring unit for indicating the value of the shemical or physical parameter to be measured of a solution contained in the test chamber, characterized in that the volume of the test chamber is variable.

16 Claims, 2 Drawing Sheets

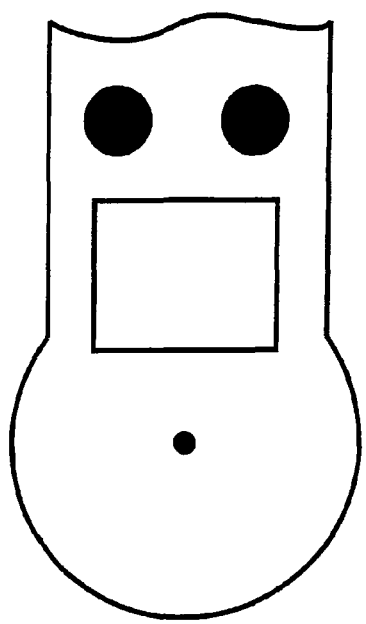
Fig. 1
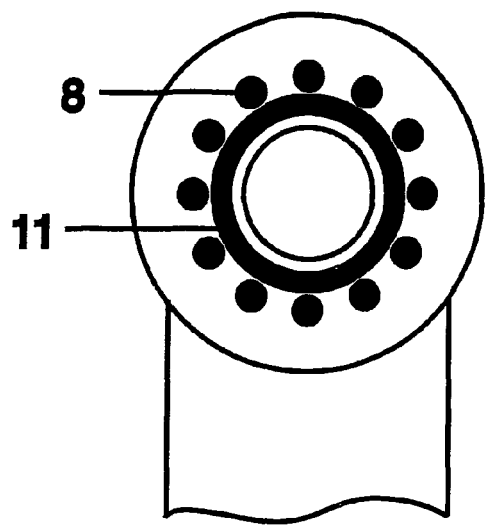
Fig. 4
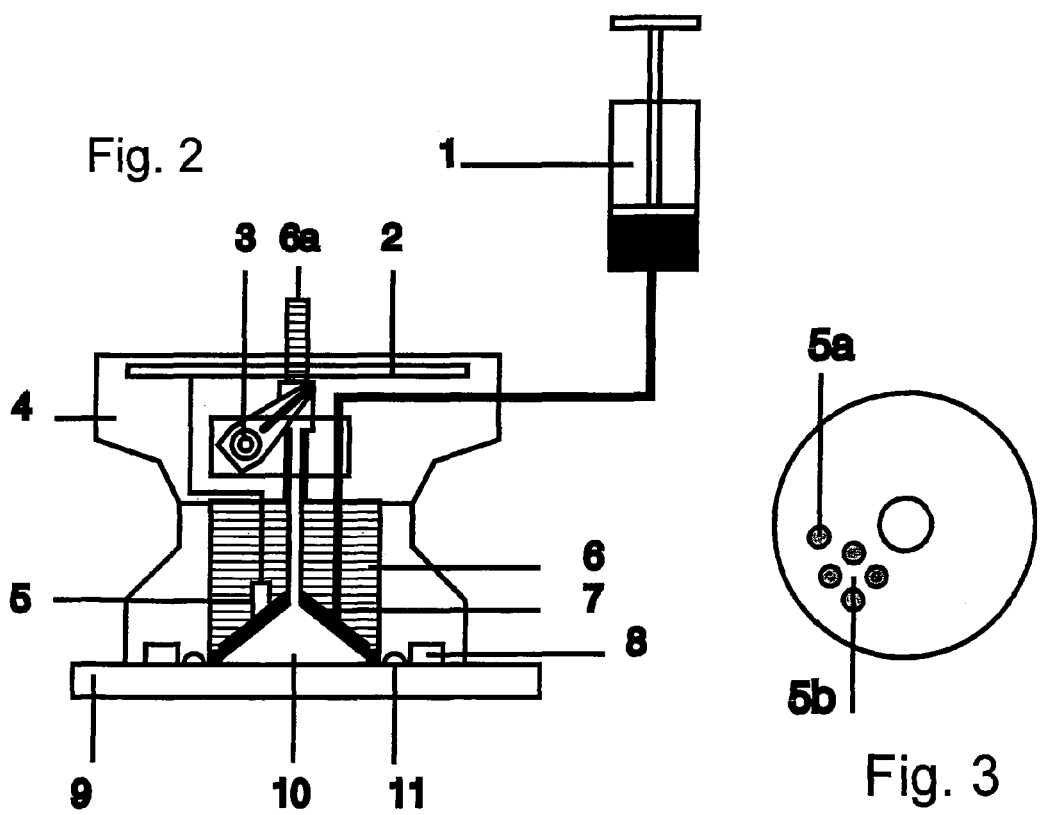
Fig. 2
Fig. 3

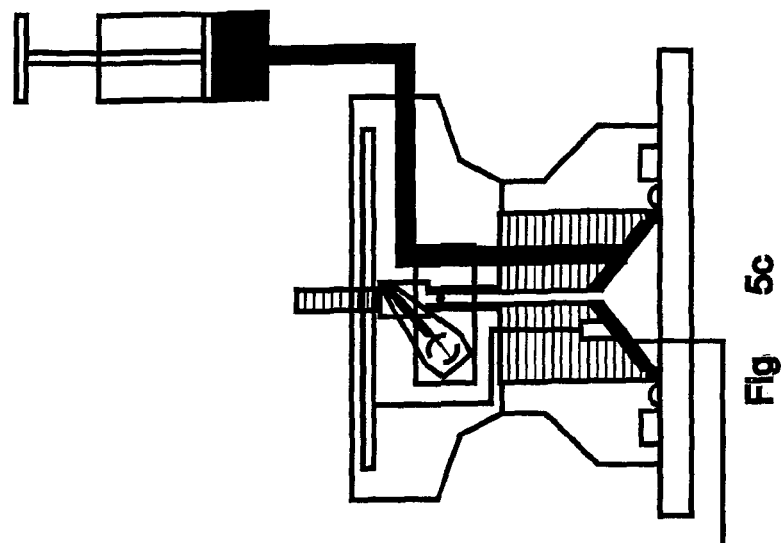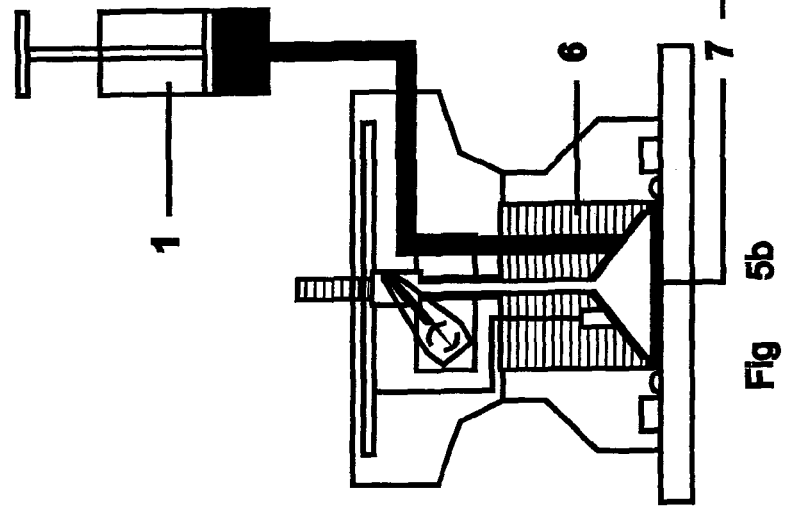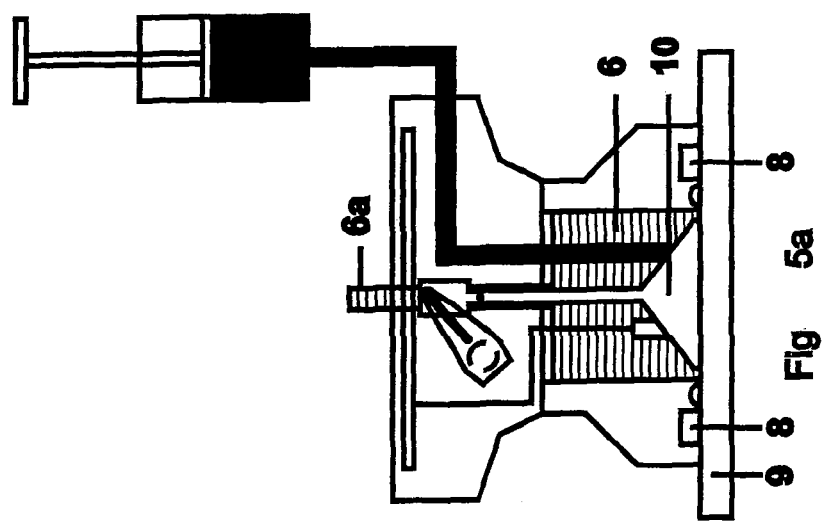

PORTABLE MEASURING DEVICE

RELATED APPLICATIONS

The present application is a 35 U.S.C. 371 national stage filing of International Application No. PCT/NL2008/000115, filed Apr. 27, 2008, which claims priority to Netherlands Application No. 1033784, filed May 1, 2007. The entire contents of each of these applications are hereby incorporated by reference herein.

The present invention relates to a portable measuring device for measuring the conductivity, the salinity, the acidity (pH) and other parameters at different types of surfaces of a measurement object such as inner and outer surfaces of tubes and surfaces of floors, walls, ceilings and such like.

The present invention relates in particular to the measuring of the salinity at surfaces of floors, walls and ceilings. The measure of salinity serves as an indicator of the measure of contamination of a surface and can be used for determining technical maintenance or treatment of the surface of a test object, for example, to determine whether a floor or wall is sufficiently clean to be coated.

A portable measuring device according to the preamble is known from the publication U.S. Pat. No. 6,946,844. This known device comprises electronic circuits, a measuring unit and a housing in which a test chamber has been formed. The test chamber is provided with a first opening that can be positioned against a test surface. The test chamber is also provided with a second opening through which a fluid such as de-ionised water can be brought into the test chamber and with a resilient seal for sealing the test chamber there where it has been brought against the test surface. The test chamber also comprises an overpressure valve. The test chamber further comprises electro-mechanical means for agitating the fluid in the test chamber. The test chamber is provided with a number of sensors that are taken up in the test chamber and are connected to the electronic circuits and the measuring unit for indicating the measure of the conductivity of the fluid contained in the test chamber.

In use the working of the known device is as follows. The measuring device is placed against a test surface of a test object whereby the first opening encloses a part, of which the area is known, of the test surface. A soft, resilient and fluid-tight seal such as a plastic or rubber ring thereby ensures that the part of the surface enclosed by the first opening is sealed off against the rest of the surface of the test object. Following, a fixed volume of fluid is introduced into the test chamber through the second opening. An electro-mechanical stirrer is used to agitate the introduced fluid so that matter such as contaminants on the test part of the surface of the test object that is enclosed by the first opening of the measuring device and of which the area is known, are taken up or dissolved in the introduced fluid of which the volume is known. Subsequently, the sensors are connected to the electronic circuits present and to the measuring unit to measure the conductivity of the solution present in the test chamber.

In a different embodiment the known device is further provided with a first reservoir for the fluid to be introduced in the test chamber, a micro pump connected to it, a vacuum pump to which a second reservoir, for the fluid that is to be sucked out of the test chamber, is connected and measurement and control means. With this embodiment a fixed amount of fluid can be introduced and the said sequence of steps for testing a surface of a test object can be performed a number of times consecutively.

There are a number of disadvantages to the known device. One disadvantage is that the test chamber cannot be made completely free of air. When introducing fluid in the test chamber, it is inevitable that some air remains in the test chamber. Air in the test chamber makes the volume of fluid in the test chamber inaccurate and influences a measurement value that is to be determined on the basis of the fluid volume. Further, air will always accumulate at the uppermost side of the measuring device so that when measuring on floors air can be present in the measurement area between the sensors and thus disturb the measurement. Another disadvantage relates to the injection of fluid in the test chamber. During injecting fluid pressure is built up in the test chamber by which a certain risk exists the leakage occurs through the seal of the test chamber or that the housing of the measuring device is pressed away from the test surface of the test object.

It is therefore an objective of the present invention to provide a measuring device according to the known type during use of which a parameter value to be measured is influenced as little as possible by the presence of air in the air chamber during the measuring.

It is another objective of the present invention to provide a measuring device according to the known type during use of which the risk of leakage through the seal of the test chamber is small.

It is yet another objective of the present invention to provide a measuring device according to the known type which is easy, quick and flexible to use for measuring chemical and physical parameters on different types of surfaces of a test object such as inner and outer surfaces of tubes and surfaces of floors, walls, ceilings and such like.

According to the present invention said objectives are achieved by a measuring device for measuring the salinity, the acidity (pH) or other chemical and physical parameters on different types of surfaces such as inner and outer surfaces of tubes and surfaces of floors, walls, ceilings and such like, whereby the measuring device comprises electronic circuits, a measuring unit and a housing in which a test chamber has been formed, whereby the test chamber is provided with: 1) a first opening that can be positioned against a surface to be tested, 2) a second opening through which a fluid such as de-ionized water can be introduced into the test chamber, 3) a resilient seal for sealing the test chamber there where it is brought against the test surface area, 4) a number of sensors taken up in the test chamber that are connected to the electronic circuits and the measuring unit for indicating the value of the chemical or physical parameter to be measured of the fluid contained in the test chamber, characterized in that the volume of the test chamber is variable.

A technical advantage is that the property of the volume of the test chamber being variable can be utilized for introducing fluid in the test chamber substantially free of air and leak-free. When introducing fluid, a part of the housing is displaced and a test chamber is thus formed. Through this the risk that air remains in the test chamber is smaller than in a case in which fluid is pumped into the test chamber. Another advantage is that the friction which is to be overcome when expanding or contracting the chamber volume is so low that the risk of an overpressure arising and the latter leading to leakage of fluid from the test chamber through the seal are greatly reduced. This technical advantage is greatest when the variable volume of the test chamber can be reduced to substantially zero before introducing the fluid as is the case in the present invention.

Another technical advantage is that by introducing fluid in the test chamber by means of varying the volume of the test chamber separate means are no longer needed for agitating the contents of the test chamber. This simplifies the construction of the measuring device.

Preferably, a part of the surface within the variable volume of the test chamber is substantially cone- or bowl-shaped. The technical advantage related to this feature is that a reduction of the volume of the test chamber to almost zero without enclosure of air can easily be achieved when parts of planes within the variable test chamber that come to lie against each other in a zero-volume state of the test chamber are substantially cone- or bowl-shaped. Any possibly present air in the test chamber can then be led towards there where it cannot influence the measurement, namely towards in or close to the (curved) apex of the cone or bowl shape.

More preferably, a number of sensors are taken up in the substantially cone- or bowl-shaped part of the surface within the variable volume of the test chamber. A technical advantage related to this feature is that during measurement the sensors are always in contact with the measurement solution in the test chamber. Another technical advantage is that during measurement the measuring device can be held in any position, which offers lots of possibilities to a user of the device.

Even more preferably, the number of sensors taken up in the substantially cone- or bowl-shaped part of the surface within the variable volume of the test chamber is four. The technical advantage related to this feature is that four-point measurements are possible. The sensors can optionally be connected electronically as exitators or as measurement points to the electronic circuits and measuring unit comprised in the measuring device. Moreover, any possible contamination of the sensors or the presence of air in the test chamber can be established. Yet even more preferably, additional sensors can be taken up in the test chamber, such as a temperature sensor for determining a possible correction of the parameter value that is to be measured.

The above-mentioned embodiments of the invention are described further hereinafter and elaborated on with reference to the accompanying drawings.

In the drawings:

FIG. 1 depicts a top view of the portable measuring device according to the invention;

FIG. 2 schematically depicts a cross-sectional view as seen perpendicular to the longitudinal direction of the portable measuring device according to the invention;

FIG. 3 schematically depicts a view of the cone- or bowl-shaped measuring chamber as seen from the underside of the portable measuring device according to the invention;

FIG. 4 schematically depicts a view of the underside of the portable measuring device according to the invention; and FIGS. 5a-c depict three cross-sectional views as seen perpendicular to the longitudinal direction of the portable measuring device according to the invention, at different times during operation of the portable measuring device.

In FIG. 1 the two black spots represent operation buttons of the portable measuring device and the rectangle represents a display screen as seen from above the measuring device.

FIG. 2 depicts the measuring device that is connected to a reservoir 1 from which fluid such as, for example, de-ionised water, can be introduced into the measuring device. This reservoir can be set to discharge a dose of a pre-determined amount of fluid to the measuring device every time. In the case of measuring salinity the fixed amount of fluid will be 3 milliliters de-ionised water in conformation with ISO-standard 8502-6, the so-called Bresle method, which applies to this use and is known to the skilled person in the art. The working of the measuring device and its co-operation with reservoir 1 is controlled by means of processing electronic means 2. The processing electronic means comprise various electronic circuits and a microprocessor. The measuring device is provided with a motor, for example a servo motor, which is taken up in the housing 4. Housing 4 comprises various sensors 5. The number and the nature of these sensors can be chosen at will. In the present embodiment, a choice has been made for a four-point measurement 5b for determining the conductivity of a solution, most preferably in conformance with ISO-standard 8502-9, in the test chamber of the measuring device. The four sensors can be connected at will as exitators or as measuring points so that any possible contamination of the sensors or the presence of any possible residual air in the test chamber can be established. In this embodiment a temperature sensor 5a has also been added so that the conductivity value that is to be measured can be compensated for the temperature at which the conductivity is measured.

Housing 4 comprises a moveable part 6 that can be shut off water-tight from the rest of housing 4 by means of two O-rings. The moveable part 6 is connected to a pin 6a of which the free end protrudes at the top side of the measuring device. The moveable part 6 can be moved manually by pressing pin 6 from above. The moveable part 6 of the housing is substantially cone- or bowl-shaped at its side that faces the underside of the measuring device. It is at this side that the test chamber is formed. The manner of forming the test chamber will be described later in conjunction with a description of a method of operation using the measuring device. The test chamber can be set to a measurement volume of 3 cm$^3$ in conformation with ISO-standard 8502-6, the so-called Bresle method, which applies to this use and is known to the skilled person in the art. Of course, other measurement volumes can also be set. The measurement volume of the test chamber can be created by introducing exactly 3 milliliters of fluid from reservoir 1 into the test chamber. The accuracy of this volume of fluid that is to be introduced determines in part the accuracy of the parameter value that is to be measured.

The fixed part of housing 4 comprises a number of magnets which, in the shown embodiment, have been provided at the underside of the measuring device. These magnets serve to clamp the measuring device onto the test surface 9 of a test object. Other suitable clamping means can be used instead of magnets.

The test chamber is formed between the substantially cone- or bowl-shaped, and facing the underside of the measuring device, side 6 of housing 4, a plunger 10 and the test object 9. In the depicted example the plunger has the shape of a cone-shaped valve of which a piston is connected at its free end to the (servo) motor 3. The surfaces of plunger 10 and moveable part 6 of housing 4 fit accurately with each other so that by making these surfaces come into contact with each other the volume of the test chamber can be reduced to practically zero. Plunger 10 can be moved up and down through its piston by means of (servo) motor 3 for agitating the fluid in the test chamber so that substances or contaminants on the test surface of the test object dissolve in or are taken up in the fluid present in the test chamber, for flushing or cleaning the test chamber, etcetera. When the measuring device is held in the orientation according to FIG. 2 during measurement, then any possible residual air in the test chamber will end up in the area around the piston of the bowl-shaped valve, at any rate at a distance from sensors 5, so that the parameter value that is to be measured is not influenced. FIG. 2 further depicts a sealing ring 11 which ensures that the test solution stays in the test chamber.

For the present embodiment in conformation with ISO-standard 8502-6, the so-called Bresle method, the contact area,—that is: the area of the test object which during measurement is enclosed between the outer circumference of plunger 10 and the outer circumference of moveable part 6 of housing 4 that is in contact with the surface of the test object—is 1250 mm². It will be clear that the magnitude of the contact area can be determined at will. For applications other than the Bresle method, this contact area can be easily set to another value, for example by replacement with a housing and a plunger that have different dimensions.

FIG. 3 schematically depicts a view of the cone- or bowl-shaped measurement chamber as seen from the underside of the portable measuring device according to the invention. In this example four sensors have been arranged in a square; other arrangements can also be applied. A temperature sensor 5a is to be seen, as well as the area 5b that comprises conductivity sensors in a four-point arrangement.

FIG. 4 schematically depicts a view of the underside of the portable measuring device according to the invention whereby a circular arrangement of the magnets 8 and the concentric position of the sealing ring 11 relative to the moveable part 6 of housing 4 and plunger 10 are to be seen.

FIGS. 5a-c depict three cross-sectional views as seen perpendicular to the longitudinal direction of the portable measuring device according to the invention, at different times during operation of the portable measuring device. The working of the portable measuring device according to the invention is as follows. When taking the measuring device into use, it needs to be connected to a reservoir 1 from which fluid such as de-ionised water can be introduced into the measuring device. Subsequently, the test chamber needs to be cleaned. The measuring device is held upside down. The plunger thereby needs to be visible to the user. A predetermined amount of fluid, for example 3 milliliters of de-ionised water, is introduced from the reservoir 1 into the space between moveable part 6 of housing 4 and plunger 10. After the introduction of fluid in the test chamber plunger 10 can be moved to and fro a number of times through operation of the servo motor in order to agitate or homogenise the fluid and to allow any present substances or contaminants to dissolve.

Subsequently, the current value of the desired parameter, for example conductivity or salinity, can be determined. If the measured value is below a threshold value, for example 5 microSiemens, then it is indicated on the operating panel, for example by means of a LED that lights up, that the measuring device is now ready for use. The steps for cleaning the test chamber just mentioned can be repeated till the nil-measurement stays below the threshold value.

During an actual measurement moveable part 6 of housing 4 is pressed down by pressing pin 6a at the top. The volume of the test chamber can hereby be reduced to almost zero. FIG. 5a depicts the measuring device in this state. After that, the measuring device is positioned with its underside against the test surface of the test object. Magnets 8 ensure that the measuring device does not shift relative to the test object.

For the actual measurement 3 milliliters of water are subsequently introduced into the test chamber. The introduced fluid effectuates that moveable part 6 of housing 4 then is pushed back upwards so that a measurement volume is formed in the test chamber. FIG. 5b depicts the measuring device in this state. By initiating software stored in the measuring device a so-called wash cycle can be performed. Plunger 10 can be moved up and down according to an adjustable pattern such that any possible solid substances on the test surface dissolve in the fluid present in the test chamber. FIG. 5c depicts the measuring device in a state in which there is maximum protrusion of plunger 10. Subsequently, the actual value of the desired parameter can be determined. This value can be read from the operating panel of the measuring device and also be stored in a memory, for example a memory of the measuring device itself, for processing later. It is to be understood that the portable measuring device according to the invention can be readily adapted to incorporate further features relating to the readings to be taken by the measuring unit. For example, the electronic circuits may comprise functions relating to storage, and optionally also analysis, of one or more readings of the measuring unit. The portable measuring device can also comprise an electronic connection port for exchange of data with an external processing device. The electronic connection port of the portable measuring device can be configured in regard of remote programming, and preferably real-time programming, of the electronic circuits and memory comprised in the portable measuring device.

The measuring device can of course also be adapted to perform a number of cycles consecutively. The measuring device can be adapted to determine any parameter of choice. The working of the measuring device can be ensured by paying attention to the position of the measuring device in which it is held while measuring. It will be clear that when measuring at ceilings any possibly present residual air in the test chamber will accumulate at the side of the test object. Similarly, when measuring at walls the measuring device will need to be kept in a position such that the side at which the sensors are located faces downwards, towards the bottom or a floor so that any possibly present residual air in the test chamber will not accumulate at the sensors and thereby disturb the measurement.

The volume of the measurement chamber being variable, the use of a plunger which mechanically fits accurately to a moveable part of the housing, and a part of the contact surface between the moveable part of the housing and the plunger being cone- or bowl-shaped are all features that ensure that the risk of enclosure of air in the test chamber during measurement is reduced to practically zero. By this the measurement values can reflect the actual values as accurately as possible.

The described embodiment of the portable measuring device according to the present invention is directed to the measurement of conductivity for determining the salinity at surfaces such as floors, walls and ceilings. It is in particular directed to performing a measurement in conformation with ISO-standard 8502-9, the so-called Bresle method. It will be clear that other parameters can also be determined through the application of suitable sensors. It will also be clear that with necessary adaptations such as adapter devices the portable measuring device according to the present invention can also be used for measurements at different surfaces such as inner and outer surfaces of tubes.

The invention claimed is:

1. Portable measuring device for measuring the salinity, the acidity (pH) or other chemical and physical parameters on different types of surfaces, whereby the measuring device comprises electronic circuits, a measuring unit and a housing in which a test chamber has been formed, whereby the test chamber is provided with: 1) a first opening that can be positioned against a surface to be tested, 2) a second opening through which a fluid can be introduced into the test chamber, 3) a resilient seal for sealing the test chamber where the test chamber is brought against the test surface area, 4) a number of sensors taken up in the test chamber that are connected to the electronic circuits and the measuring unit for indicating the value of the chemical or physical parameter to be measured of the fluid contained in the test chamber, characterized in that the measuring device further comprises means for varying the volume of the test chamber, wherein the means for varying the volume reduces the volume of the test chamber to substantially zero.

2. Method of measuring the salinity, the acidity (pH) or other chemical and physical parameters on different types of surfaces using the measuring device according to claim 1, comprising the steps of: 1) reducing the volume of the test chamber to substantially zero, 2) positioning the measuring device against a part of the surface to be tested of a test object, 3) introducing fluid from a reservoir into the test chamber of the measuring device in order to form a measurement volume in the test chamber, wherein the means for varying the volume of the test chamber comprise a plunger, whereby the fluid displaces the plunger away from its position of lying flush against the surface of the test object of which a measurement is to be taken, 4) moving the plunger up and down a number of times in order to agitate the fluid, and 5) performing a measurement.

3. Portable measuring device according to claim 1, characterized in that the means for varying the volume of the test chamber comprise a plunger.

4. Portable measuring device according to claim 1, characterized in that the variable-volume test chamber is formed between a side of the housing of the device that faces the test object, the plunger and the surface of the test object of which a measurement is to be taken.

5. Portable measuring device according to claim 3, characterized in that the plunger is displaceable by the presence of a fluid between its surface and the surface of the test object of which a measurement is to be taken.

6. Portable measuring device according to claim 4, characterized in that the volume of the test chamber is reducible to substantially zero by displacement of the plunger flush against the surface of the test object of which a measurement is to be taken.

7. Portable measuring device according to claim 1, characterized in that a part of the surface within the variable volume of the test chamber is substantially cone- or bowl-shaped.

8. Portable measuring device according to claim 1, characterized in that a number of sensors are taken up within the variable volume of the test chamber.

9. Portable measuring device according to claim 1, characterized in that a number of sensors are taken up in a substantially cone- or bowl-shaped part of the surface within the variable volume of the test chamber.

10. Portable measuring device according to claim 7, characterized in that the sensors are taken up in a four-point arrangement.

11. Portable measuring device according to claim 8, characterized in that the sensors are taken up in a four-point arrangement.

12. Portable measuring device according to claim 1, characterized in that the electronic circuits comprise functions relating to storage of one or more readings of the measuring unit.

13. Portable measuring device according to claim 1, characterized in that the electronic circuits comprise functions relating to analysis of one or more readings of the measuring unit.

14. Portable measuring device according to claim 1, characterized in that the device further comprises a connection port for exchange of data with an external processing device.

15. Portable measuring device according to claim 13, characterized in that the connection port is suitable for real-time programming of the electronic circuits and memory comprised in the portable measuring device.

16. Method of measuring a chemical or physical parameter on different types of surfaces using the measuring device according to claim 15, comprising the steps of: 1) reducing the volume of the test chamber to substantially zero, 2) positioning the measuring device against a part of the surface to be tested of a test object, 3) introducing fluid from a reservoir into the test chamber of the measuring device in order to form a measurement volume in the test chamber, whereby the fluid displaces the plunger away from its position of lying flush against the surface of the test object of which a measurement is to be taken, 4) moving the plunger up and down a number of times in order to agitate the fluid, 5) performing a measurement, and 6) storing the measured value for processing later.

* * * * *